United States Patent [19]

Herold et al.

[11] Patent Number: 5,947,117
[45] Date of Patent: *Sep. 7, 1999

[54] PRECIPITATION SYSTEM FOR A POWDER INHALER

[75] Inventors: Heiko Herold, Neuss; Axel Wollenschläger, Bergisch Gladbach, both of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/555,023

[22] Filed: Nov. 8, 1995

[30] Foreign Application Priority Data

Nov. 15, 1994 [DE] Germany .............................. 44 40 734

[51] Int. Cl.$^6$ .......................... A61M 15/00; A61M 15/06
[52] U.S. Cl. ................................ 128/203.15; 128/203.21
[58] Field of Search ........................ 128/203.15, 203.21, 128/203, 23, 203.25, 203.12

[56] References Cited

U.S. PATENT DOCUMENTS

| | | | |
|---|---|---|---|
| 2,214,032 | 9/1940 | Stewart | 128/203.15 |
| 2,653,608 | 9/1953 | Miller et al. | 128/203.15 |
| 2,992,645 | 7/1961 | Fowler | 128/203.15 |
| 4,206,758 | 6/1980 | Hallworth et al. | 128/203.15 |
| 4,907,583 | 3/1990 | Wetterlin et al. | |
| 5,033,463 | 7/1991 | Cocozza | 128/203.15 |
| 5,304,125 | 4/1994 | Leith | |
| 5,676,130 | 10/1997 | Gupte et al. | 128/203.15 |

FOREIGN PATENT DOCUMENTS

| | | | |
|---|---|---|---|
| 0237507 | 9/1987 | European Pat. Off. | |
| 0451745 | 10/1991 | European Pat. Off. | |
| 2352556 | 12/1977 | France | |
| 4239402 | 5/1994 | Germany | |
| 2248400 | 4/1992 | United Kingdom | 128/203.15 |
| 9010470 | 9/1990 | WIPO | 128/203.15 |
| 9015635 | 12/1990 | WIPO | |
| 9318811 | 9/1993 | WIPO | 128/203.15 |

*Primary Examiner*—Kimberly L. Asher
*Attorney, Agent, or Firm*—Sprung Kramer Schaefer & Briscoe

[57] ABSTRACT

The precipitation system comprises a collection tube (1) which can be fitted onto the powder inhaler with a mouthpiece (3) and a centrifugal precipitator (2,6) arranged in the collection tube (1). This centrifugal precipitator has at least one spin-producing surface (2) which produces a spin flow in the collection tube (1), as a result of which the heavy coarse powder particles are precipitated on the inner wall of the collection tube (1) while the lighter fine powder particles pass into the mouthpiece (3) due to a flow which is essentially restricted to the area surrounding the tube axis.

7 Claims, 2 Drawing Sheets

PRECIPITATION SYSTEM FOR A POWDER INHALER

The invention relates to a coarse precipitation system which can be used additionally with a suitable powder inhaler for therapy with aerosols.

BACKGROUND OF THE INVENTION

Numerous medications are administered in the form of aerosols. In the past, compressed-gas aerosols have mainly been used for this purpose. Owing to the known problems concerning environmentally harmful propellants, therapy with powder aerosols gained increasingly in importance.

In this type of drug, the active ingredient is used in a suitable formulation, e.g. in a pure form as soft pellets or as a mixture with suitable auxiliaries, e.g. lactose-monohydrate.

When inhaled by the patient, the formulation is dispersed into the stream of breathing air, only sufficiently fine particles reaching the site of action, the lung, while coarser agglomerates and particles are precipitated in the upper respiratory tracts and in the throat area.

An important objective of the development of powder inhalers and formulations is therefore to maximize the proportion of fine powder and to minimize the proportion of coarse powder.

The energy required for the dispersion of the formulation in powder inhalers is usually obtained from the stream of breathing air of the patient. According to experience, this energy, which is available only to a limited extent, is not sufficient for a quantitative dispersion into respirable particles of active ingredient.

Moreover, numerous aerosol formulations (e.g. adhesive powder mixtures) contain auxiliaries (e.g. lactose monohydrate) which, based on their grain size, are mainly precipitated as coarse powder in the upper respiratory tracts. The finer particles of active ingredient adhering to these auxiliaries are thus likewise precipitated in the upper respiratory tracts.

This is particulary disadvantageous when the active ingredient—such as, for example, in the case of corticoids—shows an undesired local effect. In the past, for instance, local fungal infections were often described as a consequence of aerosol therapy with corticoids.

In the case of compressed-gas aerosols, numerous precipitation systems, called "spacers", were described to reduce this precipitation of active ingredient in the throat area.

These precipitation systems contain a number of advantages:

Firstly, the speed of the spray jet emerging from the spray heads is reduced, as a result of which the precipitation due to impaction in the throat area is reduced.

Moreover, in particular in the case of large-volume spacers, a quantitative evaporation of the propellant can be achieved, as a result of which the droplet size of the aerosol droplets is reduced. Finally, there is the possibility, in the case of large-volume spacers, to dissociate the inhalation of the patient from the release of the active ingredient and thus to reduce the coordination problems of numerous patients.

While spacers of this type are generally in use for compressed-gas aerosols, they have not previously been used in powder aerosols. This is surprising in so far as the principle problems of the precipitation of appreciable quantities of active ingredient in the throat likewise exist in powder aerosols.

Precipitation systems which are to be used in conjunction with powder aerosols however, must have different design properties from precipitation systems such as are in use for compressed-gas aerosols.

The invention is based on the object of developing a precipitation system which is suitable for combination with powder inhalers and leads to an appreciable reduction in the depositing of non-respirable active ingredient and auxiliary in the throat area. On the other hand, the desired, respirable quantity of active ingredient is not to be adversely affected by the precipitation system.

According to the invention, this object is achieved in that the precipitation system comprises a collection tube which can be fitted onto the powder inhaler with a mouthpiece and a centrifugal precipitator which is arranged in the collection tube and has at least one spin-producing surface which produces a spin flow in the collection tube, as a result of which the heavy coarse powder particles are precipitated on the inner wall of the collection tube while the lighter fine powder particles pass into the mouthpiece due to a flow which is essentially restricted to the area surrounding the tube axis.

The flow resistance of the centrifugal precipitator advantageously lies between 0.3 mbar and 2 mbar for an inhalation flow of 60 l/min.

The collection tube advantageously has a volume between 10 cm$^3$ and 300 cm$^3$, preferably between 20 cm$^3$ and 100 cm$^3$.

The spin-producing surface can consist of a flat or curved vane surface mounted in the collection tube. However, the spin-producing surfaces preferably consist of elliptical segments which fill the entire cross-section of the collection tube, are inclined at an acute angle $\alpha$ to the tube axis, and whose periphery terminates flush with the inner wall of the collection tube.

Particularly good precipitation results are achieved if the spin-producing segment surfaces are designed such that a central opening remains in the tube centre at the inner edges of the segments.

The angle $\alpha$ between the tube axis and the segment surfaces preferably lies within the range from 400 to 700. The optimum ratio of the inside diameter of the collection tube to the diameter of the central opening lies within the range from 2 to 10.

The system described here is distinguished particularly by the following properties:

In comparison with precipitation systems according to the principle of impact precipitation, the system described here shows no appreciable inherent pressure loss in use. This prevents the volume flow in the inhaler being reduced during the application, which would have a disadvantageous effect on the dispersion of the formulation and the metering accuracy. Moreover, the flow resistance of the entire system, which is unpleasant for the patient, is not noticeably increased.

A further characteristic of the system presented is that it is distinguished by a small volume, as a result of which it differs, in particular, from spacers, such as are customary in compressed-gas aerosols. It is thus prevented that an appreciable part of the air stream inhaled by the patient is not loaded with active ingredient. Moreover, the ensuing small construction of the appliance allows it to be carried with the patient without effort.

A further advantage of the system presented here consists in the fact that it can be dismantled and cleaned in a simple manner by the patient.

SUMMARY OF THE INVENTION

Finally, a system according to the principle presented here shows no appreciable reduction in the desired, respirable fine powder when the precipitation system is inserted between the powder inhaler and the mouth of the patient, whereas systems according to the impact precipitation principle also precipitate some of the desired respirable fine powder, as a result of which the dose of active ingredient reaching the lung is reduced in an undesired manner.

BRIEF DESCRIPTION OF THE DRAWINGS

The invention is explained in greater detail below with reference to an exemplary embodiment illustrated in the drawings, in which.

Figure 1:
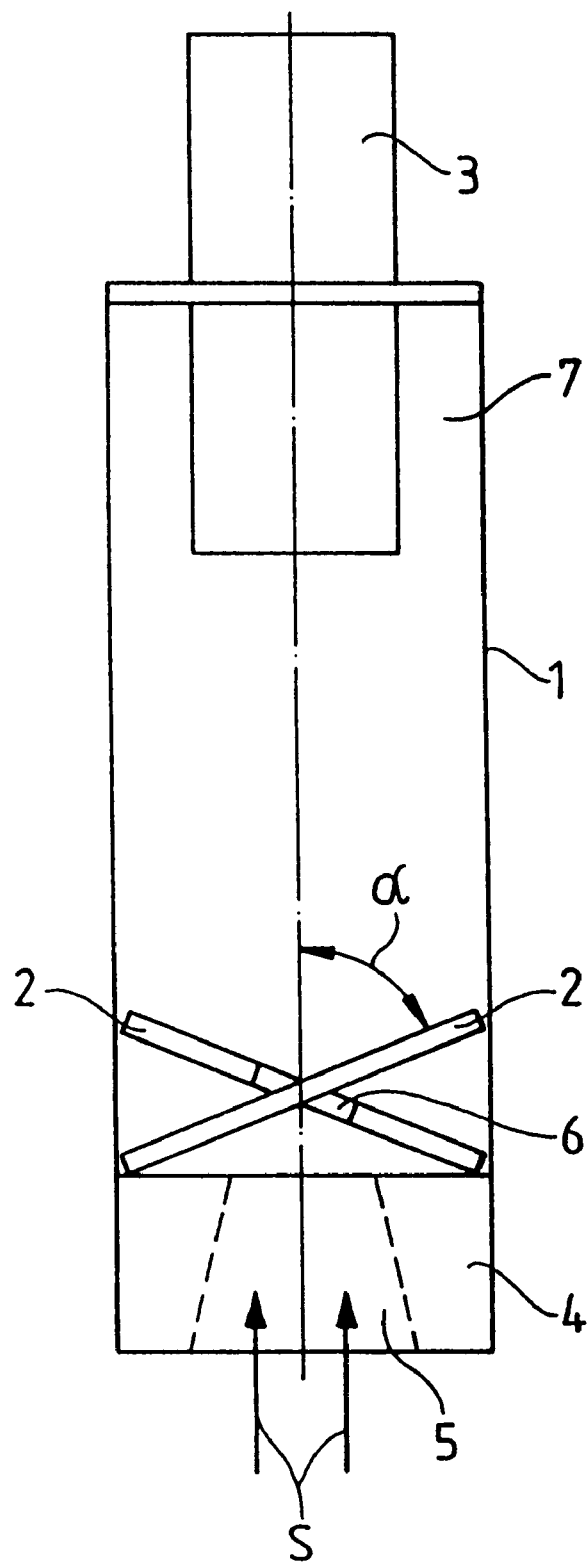
FIG. 1 shows an outline or a side view of the precipitation system.

The precipitation system according to FIG. 1 comprises a collection tube 1 with built-in spin-producing surfaces 2, a mouthpiece tube 3 at the one end and an adapter 4 at the other end. The adapter 4 is provided with a flattened-off, truncated cone-like opening 5. The opening 5 is adapted in its shape to the actual mouthpiece of a powder inhaler so that the precipitation system can be fitted with the opening 5 onto the powder inhaler. The mouthpiece tube 3, which protrudes with a part of its length into the collection tube 1, then forms the new mouthpiece for the inhaler system comprising the powder inhaler and the precipitator. The projection from the mouthpiece tube 3 into collection tube 1 forms an annular chamber 7 between itself and the inner wall of the tube.

Figure 2:
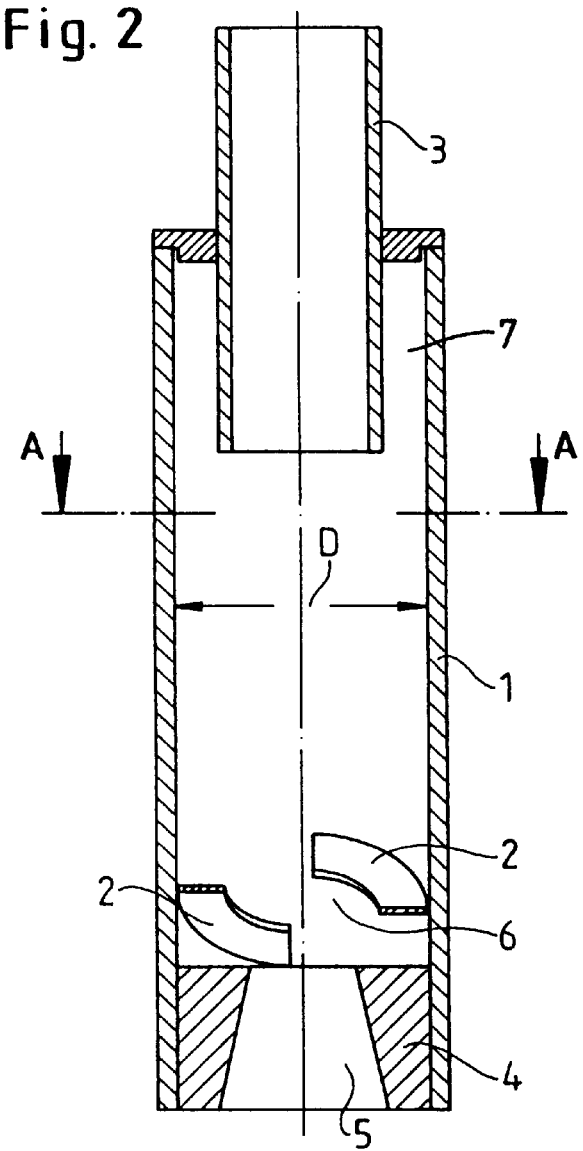
FIG. 2 shows a longitudinal section through the precipitation system.
Figure 3:
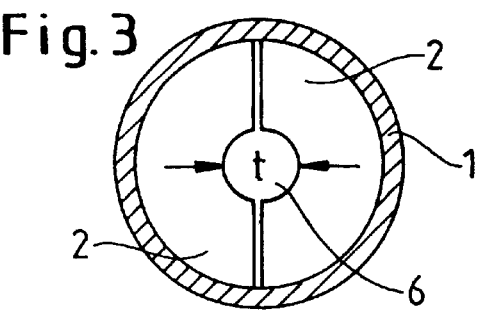
FIG. 3 shows a cross-section A—A through the precipitation system according to FIG. 2.

The spin-producing surfaces 2 are built into the collection tube 1 in an oblique position and consist of elliptical segments which fill the entire cross-section of the collection tube (see FIG. 2). The segments form, with the tube axis, an acute angle α which lies between 40° and 70° (see FIG. 1). Furthermore, the segments 2 are provided at their inner edges, i.e. in the tube centre, with a central circular opening 6.

The spin-producing surfaces consisting of the elliptical segments 2 impart to the flow, which was previously essentially axially parallel (flow arrows S), a component of spin which brings about a spiral flow in the collection tube 1. This has the consequence that the relatively heavier pulverulent particles are hurled against the inner wall of the collection tube owing to the centrifugal force, while the lighter fine powder particles pass into the mouthpiece tube 3 due to a flow which is essentially restricted to the area surrounding the tube axis. The heavy coarse powder particles are thus precipitated in the collection tube 1 which can be emptied from time to time. The classifying effect of the precipitator is improved even further by the central opening 6 on the inner side of the elliptical segments 2 because no impact precipitation of the fine powder can take place there. However, above all the flow resistance of the precipitation system is thus favourably influenced (reduced). Particularly favourable flow conditions for the inhalation can be achieved if the flow resistance of the centrifugal precipitator is between 0.3 and 2 mbar for an inhalation flow of 60 l/min. For this purpose, the following dimensioning regulations must be essentially observed:

Volume of the collection tube 1 between 20 cm³ and 100 cm³

Angle of inclination α of the elliptical segments 2 between 40° and 70°

Ratio of the inside diameter D of the collection tube 1 to the diameter t of the central opening 6 between 2 and 10.

Exemplary Embodiment

For the coarse product precipitation of a powdery aerosol, a precipitation system with an inside diameter D of the collection tube of 24 mm was connected downstream of a powder inhaler. The volume of the precipitation system was about 30 cm³. The production of spin was effected by two flat vanes which were inclined at an angle of 60° to the tube axis and whose periphery terminated flush with the inner wall of the collection tube. A central opening remained in the tube centre. The ratio of the inside diameter of the collection tube to that of the central opening was about 3.6. The pressure loss of the precipitation system was measured at 0.9 mbar for an inhalation flow of 60 l/min.

During the inhalation operations, it was possible to reduce the proportion of coarse powder leaving the precipitation system to less than 40% in comparison with the entry, the fine proportion remaining almost completely constant.

We claim:

1. A precipitation system for a powder inhaler, comprising a collection tube having a longitudinal axis (1) which is adapted to be fitted onto a powder inhaler, a mouthpiece (3) having a central opening along the longitudinal axis of said collection tube, a part of said mouthpiece protruding into said collection tube to form an annular chamber (7) between itself and the wall of the collection tube, and a centrifugal precipitator (2,6) arranged in the collection tube (1) and having at least one flat or curved vane surface (2) mounted in the collection tube which produces a spin flow in the collection tube (1), and said centrifugal precipitation having a central opening (6) along the longitudinal axis of said collection tube, as a result of which the heavier coarse powder particles present in a powder passing through said inhaler are precipitated on the inside wall of the collection tube (1) and collect in said annular chamber and do not enter the mouthpiece, while the lighter fine powder particles present in the powder are essentially restricted to flow through the area surrounding the longitudinal axis of said tube through said central opening of said centrifugal precipitator and then pass into the mouthpiece (3) through the central opening of said mouthpiece.

2. Precipitation system according to claim 1, wherein the flow resistance of the centrifugal precipitator lies between 0.3 mbar and 2 mbar for an inhalation flow of 60 l/min.

3. Precipitation system according to claim 1, wherein the collection tube (1) has a volume between 10 cm³ and 300 cm³, preferably between 20 cm³ and 100 cm³.

4. Precipitation system according to claim 1, wherein the spin-producing surface consists of a flat or curved vane surface.

5. Precipitation system according to claim 1, wherein the spin-producing surfaces consist of elliptical segments (2) which fill the entire cross-section of the collection tube, are inclined at an acute angle α to the tube axis, and whose periphery terminates flush with the inner wall of the collection tube.

6. Precipitation system according to claim 5, wherein the angle α lies within the range of 40° to 70°.

7. Precipitation system according to claim 5, wherein the ratio of the inside diameter D of the collection tube (1) to the diameter t of the central opening (6) is 2 to 10.

* * * * *